United States Patent [19]

Schenato et al.

[11] Patent Number: 5,168,477

[45] Date of Patent: Dec. 1, 1992

[54] METHOD OF AND AN APPARATUS FOR THE ULTRASONIC IDENTIFICATION OF MATERIALS AND EQUIPMENTS

[75] Inventors: Adelmo Schenato, Milan; Massimo Prazzoli, Piacenza; René Denis, Brebbia; Fereydoun Lakestani, Varese; Gian P. Battagin, Angera; Lodovico Bertani, Piacenza, all of Italy

[73] Assignee: Agip S.p.A, Milan, Italy

[21] Appl. No.: 709,711

[22] Filed: Jun. 3, 1991

[30] Foreign Application Priority Data

Jun. 4, 1990 [IT] Italy ................. 20529 A/90

[51] Int. Cl.⁵ .................................... G01S 15/00
[52] U.S. Cl. ........................................ 367/87
[58] Field of Search ................... 367/87; 340/543

[56] References Cited

U.S. PATENT DOCUMENTS 4,280,119 7/1981 May ........................ 340/543
4,342,549 8/1982 Lemelson .................. 425/150

FOREIGN PATENT DOCUMENTS 0250340 12/1987 European Pat. Off. .
2570533 3/1986 France .

Primary Examiner—Daniel T. Pihulic
Attorney, Agent, or Firm—Shea & Gould

[57] ABSTRACT

A system of identifying materials and equipment consisting of small metal plates applied to them on their concealed surface and in which identifying means are provided consisting of incisions or blind holes which are detected under scanning or by multiplex technology using ultrasonic transducers which emit ultrasonic waves and which detect the ultrasonic signals reflected by the concealed surface, which set up a different binary coded sequence of return signals as a function of the markings made on the concealed surface of the small plate which is applied to the material.

18 Claims, 6 Drawing Sheets

FIG.1A
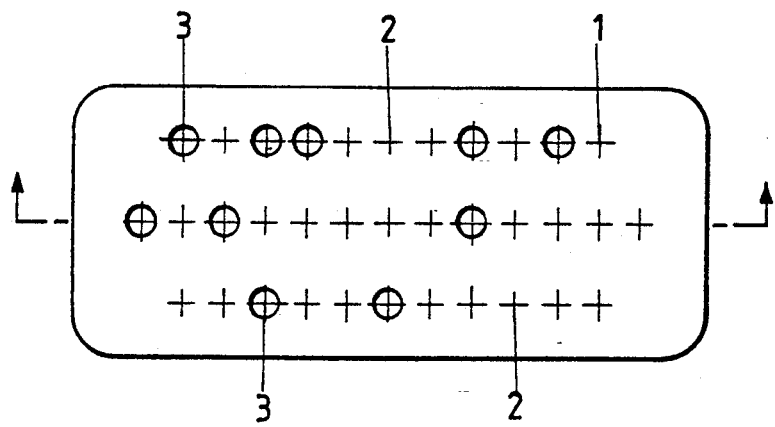
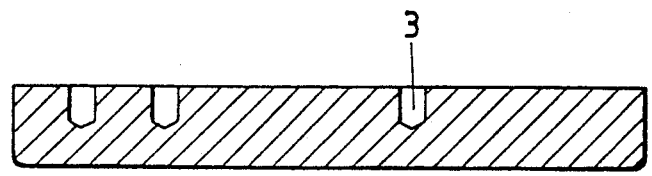
FIG.1B
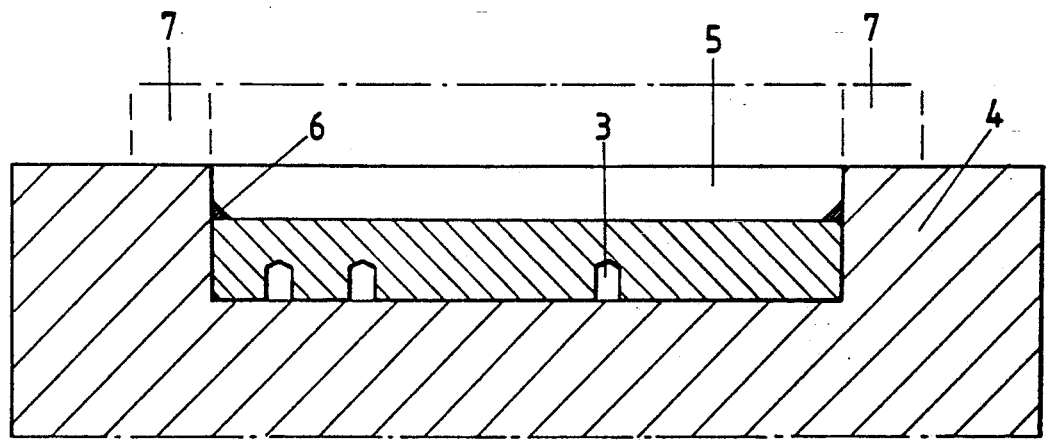
FIG.1C

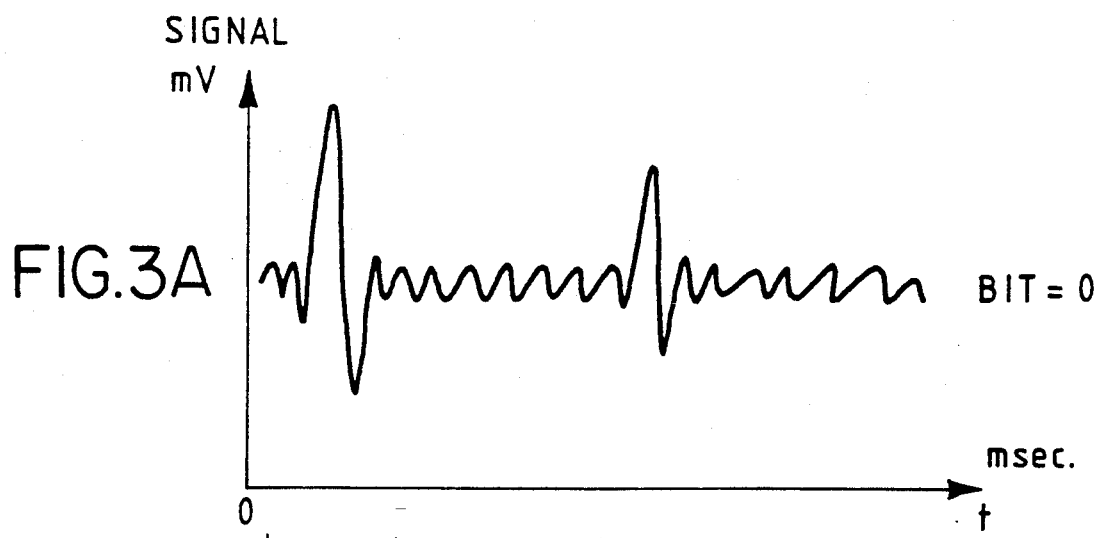
FIG. 3A
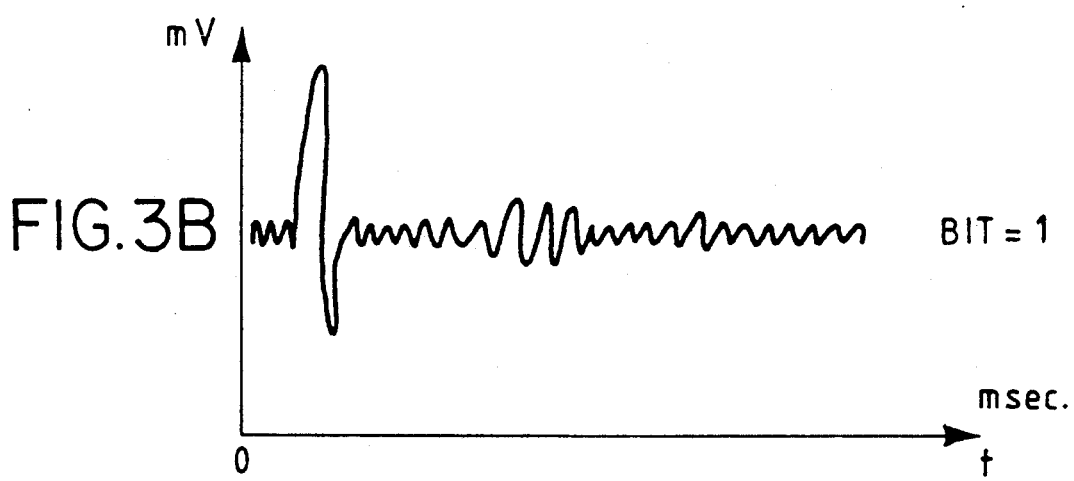
FIG. 3B
FIG. 4
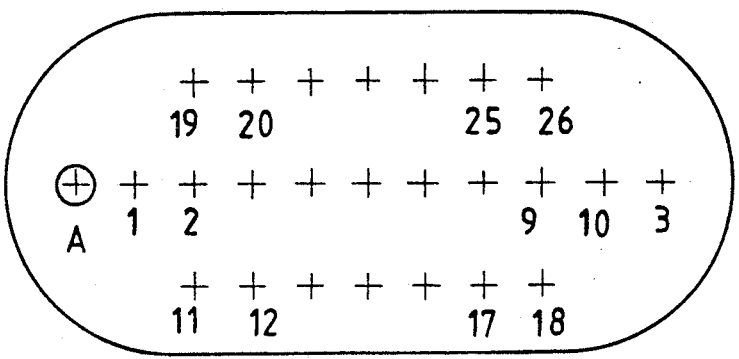

METHOD OF AND AN APPARATUS FOR THE ULTRASONIC IDENTIFICATION OF MATERIALS AND EQUIPMENTS

DESCRIPTION

The object of the present invention is the identification of materials and equipment and it is particularly adapted to the identification of those materials and equipment to which it is not possible in practice to apply conventional recognition means by virtue of the particularly onerous conditions under which they are used.

In the present description, we refer to petroleum drilling equipment, with the explicit statement that the method and the apparatus according to the invention may be used advantageously for other materials and equipment even in other sectors of industry in which demands are similar to those of the mining industry in general and the petroleum industry in particular.

The identification of petroleum drilling equipment nevertheless constitutes one of the most difficult applications of the invention, both in terms of the extremely hazardous conditions under which the said equipment operates and by virtue of the tremendous number of individual items which constitute any line-up of equipment which has to be identified or by virtue of the reliability which is required of the system, on pain of economically quite serious consequences. In the mining industry, oil drilling probes, whether they are concerned with exploration or the exploitation of fields, use equipment comprising drilling assemblies consisting of a large number of rods connected in series and with an end bit driven by an above-ground plant at a distance which may often be of several thousand metres. The rotary couple generates a considerable torque in the rods of which the assembly is composed; the forward thrust is provided by the actual weight of the assembly and, by means of a suspension system, it can be partially or totally applied to the bit. The said weight may be quite considerable, according to the length of the rod assembly.

The rods which constitute the drilling gear are added to it as the drilling proceeds downwards, in order progressively to increase its length.

The assembly operates under fairly serious conditions of mechanical and environmental stresses, at elevated temperatures and pressures and under conditions which are subject to fluctuation. During drilling, the rod assembly is withdrawn and reintroduced many times, before splitting and then recomposing it, in order to continue drilling.

Should a rod which is part of the assembly give way, there may be rather serious consequences such as a complete loss of all gear below the broken rod and abandonment of that part of the bore hole which has already been drilled.

The parts which go to make up the assembly differ from one another: apart from the already mentioned bit, there are rods of standard length but which are of different type, weight, material and diameters and also short connecting and reducing elements, weighting elements and so on. All these components, in a very precise sequence designed according to the hole which is to be bored, are connected in series to constitute the drilling assembly.

Such components are used many times in different wells and on different sites, with periodic inspections and possible reclassifications and maintenance.

The equipment which has already been used in "difficult" drilling operations may be intended for others where the risks are less great, while equipment which has been less heavily stressed previously will be allocated to "difficult" drilling jobs.

Every one of these elements has to be identified accurately and not only for the above-mentioned parameters but also for its entire previous history in terms of service and maintenance.

Every component is therefore recorded in a preferably computerised file in which are recorded all the events in its working life, along with its structural characteristics.

When it comes to using it, taking it from the store and prior to installing it in the probe, the material must be identified to verify its compliance with the requirements for the new use for which it is intended. The identification meets various demands: it is carried out both to ensure that the sequence of components in the assembly meet the requirements, and also to store the details of the components in the memory, and finally it is required for administration of the drilling operation.

The same operation of identifying and recording is carried out at inspections and at any maintenance.

It is obvious that the conventional recognition means, for example incisions or identification plates with numerical characters or externally applied bar recognition means, even if they are in positions which are less exposed to damage, are not in this case practical in that during the course of drilling the said means are exposed to shocks, vibrations, erosion, incrustation so that after a certain period of use, it would no longer be possible to recognise them. The use of ferrous materials for the drilling rods means that it is not practical to identify them by supports of a magnetic nature.

The identification of equipment and materials is according to the present invention carried out with a small plate applied thereto and marked on its concealed surface, which is then "read" by an ultrasonic transducer.

The apparatus for and method of identification will now be described with reference to FIGS. 1, 2 and 3 of the drawings which illustrate a typical embodiment which is indicated by way of illustration but which implies no limitation.

BRIEF DESCRIPTION OF THE DRAWINGS

FIGS. 1A-1C show an identification plate utilizing the present invention;

FIGS. 3A-3B illustrate the pattern of reflection of a signal in the cases of absence and presence of incisions on an identification plate;

FIG. 4 discloses an alternate embodiment of the present invention; and

Figure 2A:
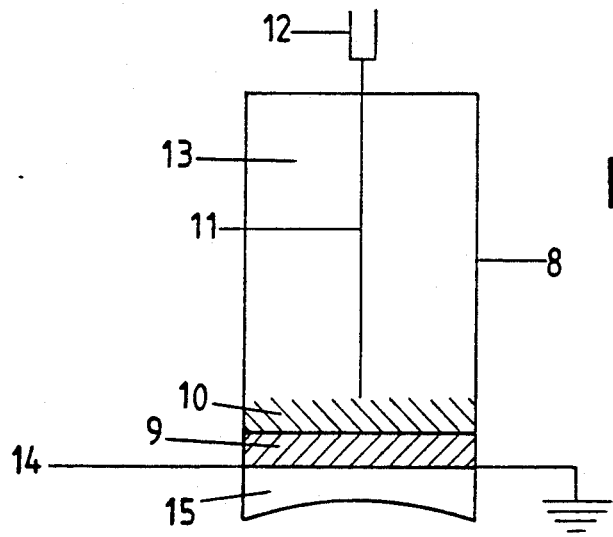
FIGS. 2A-2C show transducer arrangements for reading an identification plate of the present invention.

The identification plate 1 is preferably but not necessarily of a regular shape, for example it may be rectangular with rounded edges and may be of a material which will resist the working conditions, such as stainless steel or metallic alloys of similar performance and mechanical workability.

On one of the faces of the plate 1 there are provided, for example by mechanical working, a series of incisions of identical form and in predetermined positions 2, in each of which it is possible to provide or otherwise make the incision 3 itself. In the embodiment shown in FIG. 1, the incisions 3 are in the form of a blind hole but could equally well have any other form such as for example that of a rectilinear groove obtained by milling. The blind hole however constitutes a preferred embodiment which makes for easy machining and a greater density of data on the plate 1.

The distance between the marking positions 2 is, as will be illustrated hereinafter, determined by the dimensions and accuracy of positioning of the sensors which constitute the recording means and it constitutes a few millimetres distance between axes of the holes 3.

The bottom of the hole is preferably conical, spherical or other shape than flat.

The series of holes 3 which are absent or present according to the positions 2 constitutes the binary data for identifying the material or equipment. With N positions available, the possible combinations are equal to $2^N$ and for example the decimal value of the binary number of 16 bits or characters corresponds to the serial numbers from 0 to 65535 whereas with 32 bits it extends to far beyond 4 thousand million.

The plate 1 which is thus marked is fixed to the material 4 in which a cavity 5 shaped to match the shape of the plate 1 has been provided. The bottom of the cavity 5 must preferably extend parallel with the face of the plate 1 so that the inscribed face of the plate may be positioned parallel with the bottom of the cavity 5. The inscribed face of the plate 1 is directed inwardly so that it is protected while the face which is not inscribed is that which faces outwards.

The plate is fixed in the cavity in such a way that it cannot be moved. It may be fixed by conventional welding or by using a laser which produces smaller welds or it may be force fitted into the cavity while hot or it may be fixed with adhesives capable of withstanding the working conditions during drilling. Even if there is any penetration of liquids, solids or suspensions into the interstices of the inscribed surface due to any discontinuity in the connections between the parts, there will nevertheless be no substantial consequences for the recorded data. The cavity 5 is made to a depth greater than the thickness of the plate 1 so that the cavity remaining after installation of the plate 1 constitutes an invitation accurately to fit and position the recording means.

Along the edges of the cavity 5 it is also possible to provide a raised portion 7 which imparts greater depth of protection to the cavity.

As stated above, it is not necessary for the plate 1 or the cavity 5 to be of a regular shape, although this is a condition which facilitates construction and implementation of the invention. The adoption of non-symmetrical forms makes it possible for example mechanically to avoid the possibility of different mirrored positionings of the parts in respect of each other which, in the case of symmetrically shaped plates, requires instrumental monitoring using one or more of the positions or bits available on the plate.

According to the present invention, "reading" of the plate 1 which is fixed in the cavity 5 is carried out by scanning, position by position, the existence or not of a cavity by using ultrasonic waves emitted by transducers which emit the ultrasonic waves and record the echo reflected therefrom.

In the absence of a bore hole—and the phenomenon is the same whether the aperture is in the form of a groove or any other kind of incision—the signal is reflected onto the flat concealed surface of the plate and returns to the transducer giving an echo of appreciable intensity whereas if a bore hole is present, the conical or spherical shape of its bottom disperses the signal in all directions and the echo reflected to the transducer is only a little greater than the bottom "noise".

Ultrasonic transducers-recorders are known in the art and may be used in the present invention; for example, the transducers according to Italian Patent No. 1148549 and French Patent No. 2570533 in the name of EURATOM may be mentioned as examples. FIG. 2A shows a diagram of an ultrasonic transducer 8 which is used for the apparatus according to the invention.

The core of the ultrasonic transducer 8 consists of a piezoelectrical ceramic chip 9 capable of generating an ultrasonic signal when subjected to an electrical pulse and vice versa of generating an electrical signal when subjected to an ultrasonic pulse. By way of example, this may be obtained by complex salts of lead such as lead zirconates and titanates, currently termed PZT. In contact with one of the faces of the chip 9, the upper face in FIG. 2A, there is a coating 10 of dust of a conductive metal such as powdered tungsten, coated in resin such as epoxy resin, with a high concentration of metal in order to obtain a good level of electrical conductivity in it. The coating 10 functions either as an electrical conductor or an echo damper so that the signals are sharp and are not needlessly protracted.

Inserted into the coating 10 is an electrical conductor 11 provided with a connector 12 for extracting and supplying electrical signals, encased in a prismatic body 13 of non-conductive synthetic resin, for example epoxy resin, from which emerges the end part of the conductor 11, from the part opposite the chip 9. On the other hand, on the other face of the chip 9, the underside in FIG. 2A, there is a plate 14 of electrically conductive metal which is connected to earth.

According to a preferred embodiment of the invention, there is applied to the metal plate 14 a further coating of resin 15 which is machined so that its outer concave surface forms an ultrasonic lens to focus the ultrasonic signal generated by the chip 9 at any desired distance.

The transducer is earthed by the plate 14 and is connected by the connector 12 to an electrical pulse generator in order to generate ultrasonic waves in the transducer 8, and to an instrument for measuring the voltage—or potential—of the electrical signal generated in the transducer when it is subjected to a reflected ultrasonic signal.

The "reading" of the concealed face of the plate is, as mentioned above, based on the reflection or otherwise of the ultrasonic waves emitted by the transducer and the recording of a return signal greater than a specific threshold as the absence of a bore hole and a lesser signal which shows the presence of a bore hole. The amplitude of the echo in the presence of a bore hole is less than one tenth the amplitude of the echo when no bore hole is present.

The phenomenon is illustrated in the diagrams in FIG. 3 which illustrate the pattern of the reflection of the signal in the cases of absence and presence respectively of the bore hole.

The reading method consists of recording for each individual transducer and in a predetermined chronological order, the amplitude of the signal obtained at the time gate set to the propagation time of the sound wave which passes through the middle in both directions, currently referred to as the "flight" time corresponding to the reflection on the hidden surface of the plate.

The said value is compared with a threshold value preset at the moment the transducer is calibrated, each "bit" or position being attributed the value 0 for echoes greater than the threshold value (no bore hole) and the value 1 for lesser echoes (bore hole present), or vice versa.

Another time gate is set to the echo emanating from the visible surface of the chip in order to check that the absence of the signal in the first gate is not due to any fault in the transducer or its connection to the plate. The amplitude of the signal in the second gate is 50-60 times that of the noise level.

The everyday term 'time gate'—understood as being the interval of time in which the recording is made—refers to the fact that the ultrasonic signals reflected on the two surfaces of the plate, the visible surface and the concealed surface, are offset in time in that the two reflected signals travel paths of different lengths although proceeding at the same speed. The reflected signals therefore return to the transducer at different times, the first signal to return being that reflected from the visible surface while the second is that reflected by the concealed surface, with delays which can be determined as a function of the thickness of the plate traversed. In the event of there being two consecutive reflected signals, the order in which they present themselves is fairly significant: the reflected signal which is the first to appear is that which has travelled the shortest distance, of course through the same medium.

In ultrasonic recording technology, it is current practice to use "time gates", which tend to record signals only during the interval of time in which the said signals have the required meaning while on the other hand overlooking the signals which occur in the intervals of time in which they assume another significance which is not relevant for the purposes of the measurement to be performed.

In the case of the present invention, as shown in FIG. 3, two time gates are used.

In order of time, there is a first time gate which corresponds to the return of the ultrasonic signal reflected by the visible surface of the plate; according to a preferred embodiment of the invention, this signal is used for verifying that the system is functioning correctly, for verifying that the other recording provides reliable data, in other words that relating to the second time gate in order of the appearance time corresponding to the return of the ultrasonic signal reflected by the concealed surface of the plate.

It is not however stated that the two recordings are computed in the same sequence; in fact, it is also possible firstly to record the signal relative to the second gate and then that of the signal relative to the first gate, according to the control logic a priori or a posteriori indiscriminately, the recording of the signal correctly reflected by the visible surface being used respectively as a means of qualification or as an approval.

In the diagrams of the reflected signals in FIG. 3, the top diagram relates to the bit equal to 0, in other words the absence of a bore hole, in which corresponding to the first time gate the signal reflected from the visible surface of the plate is recorded while the signal reflected by the concealed surface is recorded at the second time gate.

The bottom diagram on the other hand refers to the bit equal to 1 and therefore to the presence of a bore hole: at the first time gate there is always the signal reflected by the visible surface while at the second there is no significant signal, in a time midway between the two gates it is possible to observe a certain low amplitude disturbance due to the defracted signal dispersed by the conical bottom of the hole.

If holes or marks with a flat bottom parallel with the surfaces of the plate were to be used, the bottom of the hole would constitute a wall to reflect the sound signal and the presence of the bore would give rise to a reflected signal which would return to the transducer in a time gate set for a time midway between the two time gates corresponding to the return of the signal reflected by the two surfaces of the plate. The use of bore holes with a dispersive bottom therefore constitutes a more simple and economic embodiment of the invention.

The recording may be carried out either with a single focusing transducer with a mechanical scanning facility, that is to say a transducer capable of exploring in accordance with a predetermined sequence the various available positions, both with an electronic scanning multi-element transducer, that is to say for simultaneous exploration of all the positions with a number of recording elements equal to the number of positions and then, in a predetermined sequence, correlating all the data from the simultaneously available positions, also by the technique currently referred to as "multiplex".

In the ensuing description, we make reference to technology involving electronic scanning, with the explicit note that mechanical scanning is a conceptually equivalent version of the method according to the present invention.

The multi-element transducer consists of a plurality of individual transducers sensitive to ultrasonic waves—of the type described hereinabove, equal in number to the available positions and disposed in the same way, that is to say the said multi-element transducer being positioned opposite the plate, each individual transducer corresponds to a bore hole position and is capable of registering the presence or absence of the concealed bore hole underneath.

Errors in positioning of the transducer and variations in the depth of the bore hole of the order of tenths of a millimeter do not compromise the accuracy of identification.

Figure 2B:
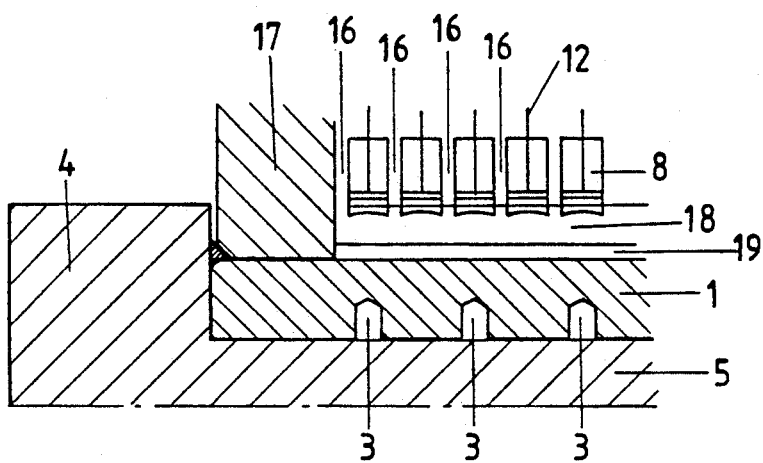
Figure 2C:
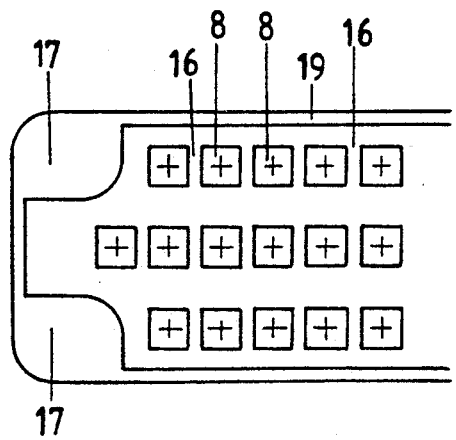

With reference to FIG. 2B which shows a transducer adapted to match the plate shown in FIG. 1, the multiple transducer consists of three parallel lines respectively of 11, 13 and 11 individual transducers disposed side by side so that they can record the presence or absence of holes in the marking of the plate on the corresponding lines.

The transverse dimension of the transducers may be fairly contained. It may assume values of a tenth of an inch (2.54 mm)—which corresponds to the pitch of the drilling—so that the 32 drilling positions may be contained in a rectangle of less than 10 $cm^2$, by way of indication 35×15 mm. The said dimension can be subsequently reduced by miniaturising the components, but already such values of drilling pitch ensure a lesser bulk of the marking means.

The individual transducers 8 in FIG. 2A are positioned one beside another in an arrangement consistent with that of the plate in FIG. 1, there remaining between them a gap 16 which is filled with resin to create a stable block of transducers which are in a fixed position.

According to a preferred embodiment of the invention, the metal plate 14 is applied to the block which is thus formed in that the said plate is glued onto the whole surface of the block and in that it is earthed so that all the transducers in the block have the same electrical reference potential.

The plan view disposition of the multiple transducer is consistent with that of the plate 1 and it has in its four corners spacers 17 which lean on the visible surface of the plate to ensure that the end faces of the transducers 8 all have their focusing lenses 15 disposed at a predetermined distance from the visible face of the plate 1.

The gap 18 between the multiple transducer and the visible face of the plate 1 is filled with a gel which has good ultrasonic transmission characteristics. A retaining edge 19 constitutes the surface which merges with the edges of the cavity 5 in FIG. 1 and it serves to retain acoustic connecting gel. As previously illustrated, the transducer functions either as a signal emitter or as a signal receiver, being capable of transforming an electrical signal into ultrasonic waves or in contrast of transforming an ultrasonic signal into an electrical signal.

Coupling of the transducer to the plate is achieved via a gel coating a few millimeters thick. For this purpose, the base of the multiple transducer is in contact with the visible face of the plate at four peripheral points via the spacers 17.

The lens 15 focuses the ultrasonic beam from each element on the depth of the bottom of the marking holes. The elements of the multiple transducer operate as emitters and receivers.

Measurements may be carried out by scanning or by the so-called multiplex technique whereby the various elements are selected in sequence.

Various "multiplexing" solutions are possible, based either on the emission-reception switching of each element of the multiple transducer or on the switching of purely reception, all the elements being energised in parallel.

The reading process consists simply of collecting and translating the properly collected echoes, distinguishing the 0 values from the 1 values. Such sequences of values constitute the data to be gathered, stored in the memory and made available to the user.

The apparatus is advantageously produced with microprocessors and other electronic components imparting it with a memory for the data collected and to be displayed and to be returned to the file containing records of the drilling materials and equipment.

It is also possible advantageously to use in the apparatus position sensors which signal to the operator whether the reading head, consisting of the multiple transducer, has been correctly positioned over the plate, monitoring sensors which verify that corresponding to the first monitoring gate the signal indicates correct functioning of the transducer, sensors which verify the memorising of the data collected, and other accessory components. The apparatus may furthermore be connected to apparatuses for monitoring the sequence and specification of the components of the assembly to ensure that they are in accordance with the plan and that there are no errors in the composition, and also that they comply with the recorded data. Recovery of the data memorised may be periodical or in real time.

EXAMPLE 1

The identification apparatus has been tested for certain components of the drilling material and in particular for:

| lightweight drilling rods with: | |
|---|---|
| 8 code numbers per connection type | (3 bits) |
| 5 code numbers per diameter and linear weight | (3 bits) |
| 4 code numbers per material | (2 bits) |
| heavy drilling rods with: | |
| 5 code numbers for nominal diameter | (3 bits) |
| weighting rods for the bit: | |
| 22 code numbers | (5 bits) |

The number of specimen to be identified for each type of component is 60,000 and therefore the serial number is defined by 16 bits; 2 bits are used for identifying the type of equipment and another 2 bits are used for monitoring the correct positioning of the reading head. In total, the number of bits required is equal to 26 which corresponds to the maximum required by the lightweight drilling rods apart from the bits required for positioning. The plate containing the said data is shown in FIG. 4. It has three parallel lines of respectively 8, 12 and 8 positions available for holes.

The plate is made from AISI 316 steel 4.5 mm thick. It is rectangular in shape and has chamfered corners measuring 36×16 mm, with the shortest side following a circular pattern.

The two data points A and B are those used for checking the correct positioning of the reading head, particularly at point A there is a bore hole with a conical bottom while there is no marking at point B. Reading is carried out in the numerical order of the positions.

The lines are spaced apart by 5.08 mm (2 tenths of an inch), while the holes have a pitch of 2.54 mm, a diameter of 2 mm, a depth of 2.5 mm and a 120° conical flaring. This can easily be produced in an automatic numerically controlled machine which can be programmed for the drilling positions of the various plates to be produced.

The apparatus and the method according to the invention lend themselves to an operation employing dedicated mini-computers or mini-processors.

EXAMPLE 2

Figure 5A:
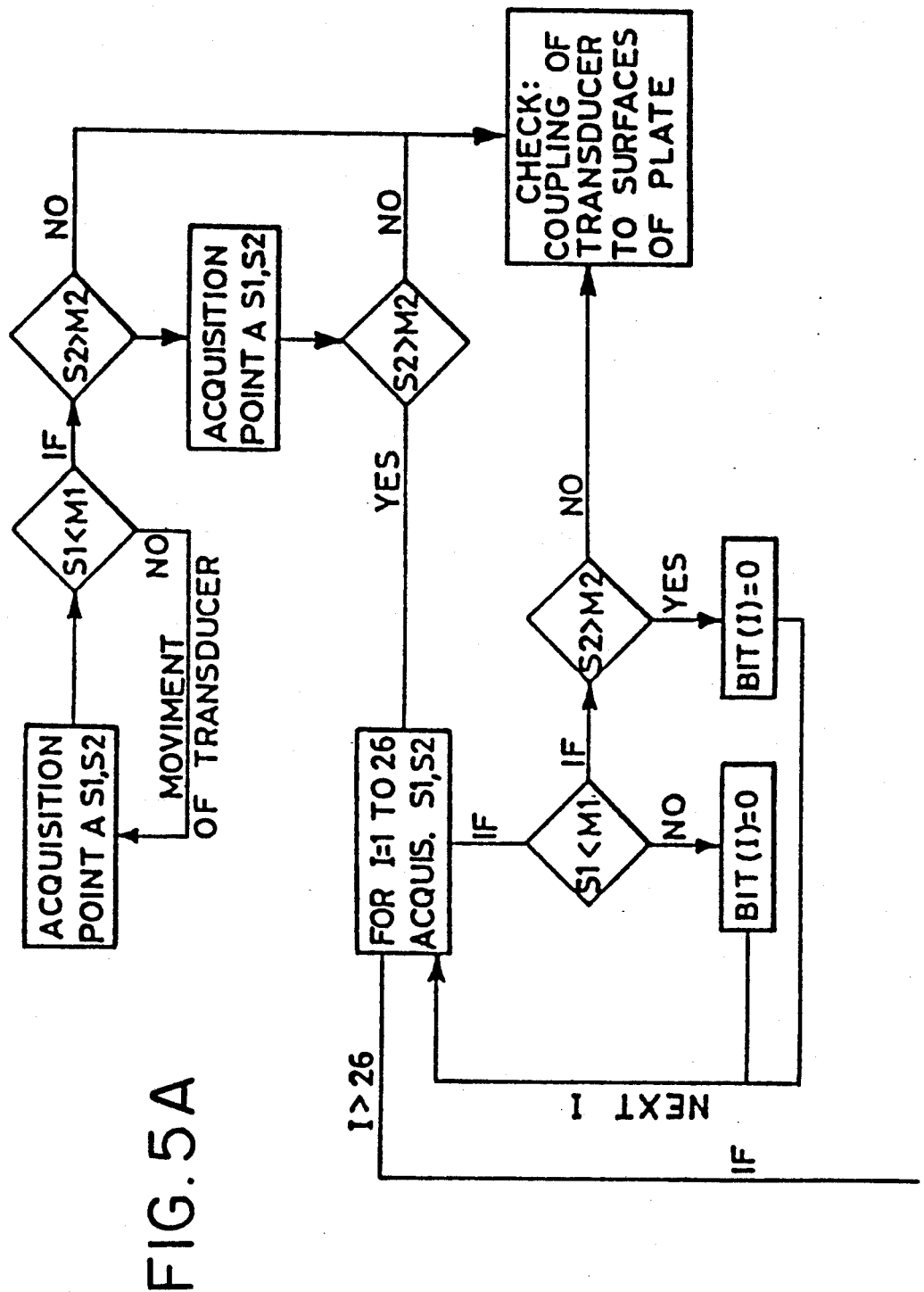
FIG. 5A, 5B, 5C illustrates a flow chart for performing the present invention.
Figure 5B:
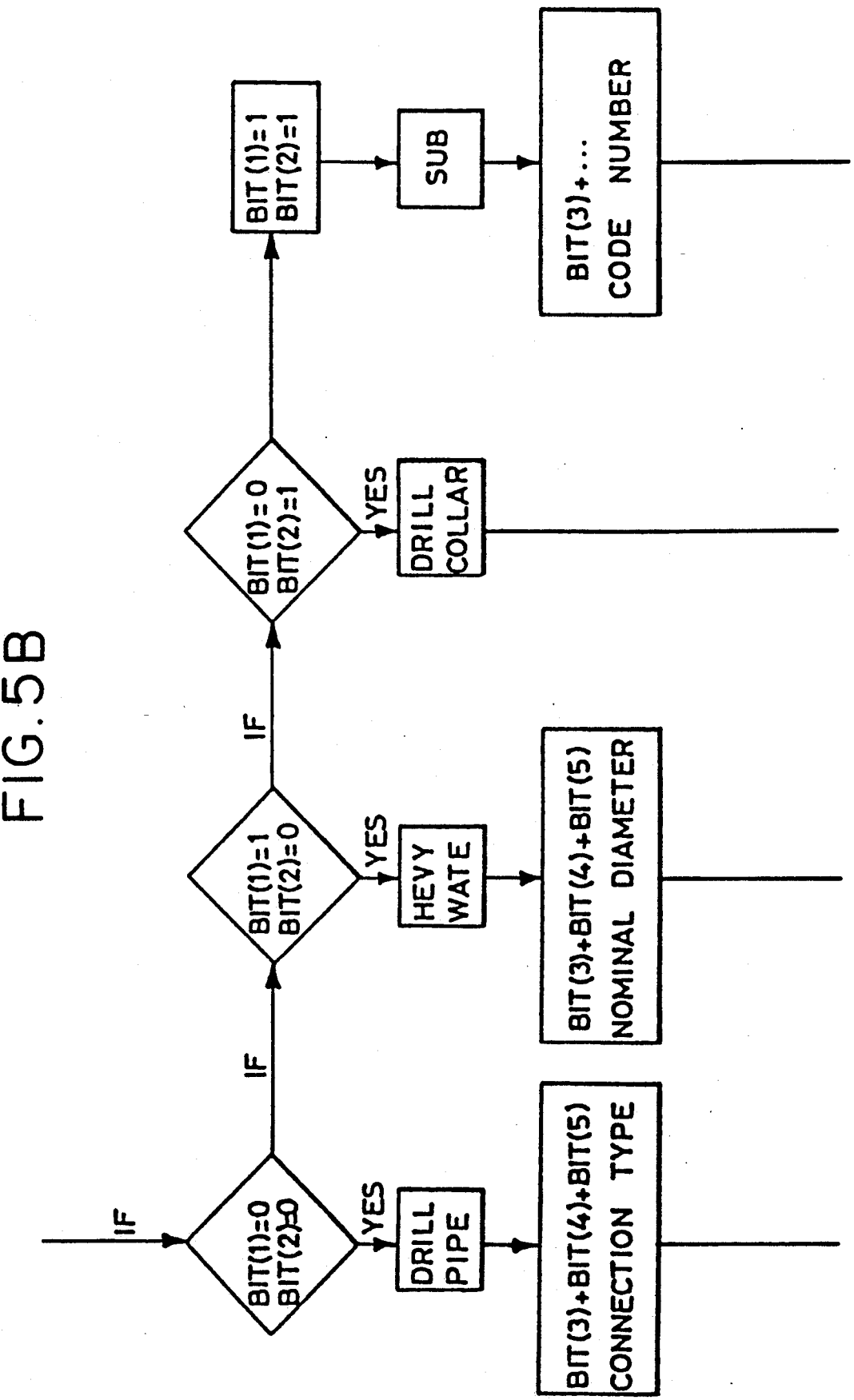
Figure 5C:
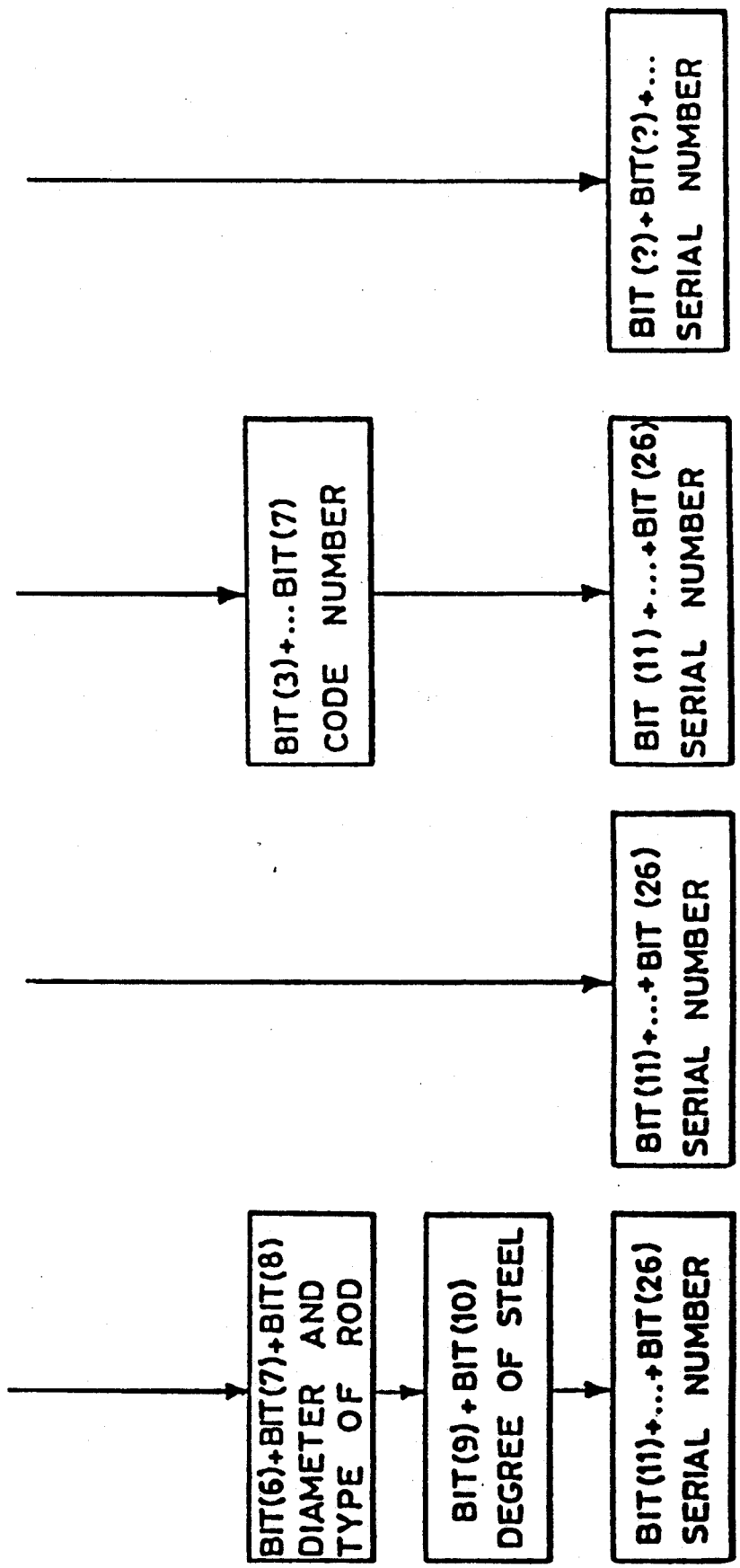

FIG. 5 shows the logic diagram of an identification programme in which the anglo-saxon terms of the petroleum technology:

| drill pipe | represents | lightweight rod |
|---|---|---|
| drill collar | represents | weighting collar |
| hevy wate | represents | weighted rod |
| sub | represents | connection | and the other terms are normally used in programming.
The symbols have the following meaning:
S1 amplitude of the signal at gate 1
S2 amplitude of the signal at gate 2
M1 threshold value of the signal at gate 1
M2 threshold value of the signal at gate 2
A,B verification of transducer position.
In Example 1, the connection has not been taken into consideration but it can be established that the two type identifying bits make it possible to identify four types of element so that they are also adequate for the connection.

The first part of the programme is a standby "loop" to check whether the reading head is correctly positioned on the identification plate or whether the first transducer is positioned so that it corresponds to the point A (it may be positioned on B by mistake).

If this condition is satisfied, the second part will automatically be carried out.

For each of the 26 points of information, in chronological order, there is obtained a value 0 or 1 from the corresponding bit, always monitoring the absence of an echo at the gate 1 (the value of the bit equal to 1) as not being due to a fault in the transducer element or its coupling.

Having defined the reliability of the connection, one passes on to the third part of the programme in which there is firstly an identification of the type of element then a reading of the codes which characterise it and then a calculation of the serial numbers of the codes which characterise it (from bit 11 to bit 26).

The apparatus and the method according to the invention are therefore advantageous also for those applications which require the marking and identification of materials and equipment which, apart from the seriousness of their use, must be capable of being "read" only by qualified persons in possession of a reading instrument and the relative codes.

The invention is useful also by virtue of its application to the field of security in identification and if required recording the carriers of plates and possibly the carriers of reading instruments.

We claim:

1. An apparatus for identifying materials and equipment by means of ultrasonic waves, comprising a marking element applied to said materials and a recorder of the said marking, characterized in that the marking element consists of a plate which is inscribed on one of its surfaces by incisions made or otherwise formed in predetermined positions to form a sequence of 0 or 1 bit corresponding to the incisions present or absent in such positions or vice versa, the said plate being fixed to the material to be identified with its inscribed surface concealed and with the opposite surface visible and in that the recorder of the marking consists of one or a plurality of ultrasonic transducers, to be positioned opposite the positions of the markings on the plate, which are energized by an electrical signal to generate an ultrasonic signal which is reflected on the concealed surface of the plate and which returns to the transducer to generate a different return electrical signal as a function of the presence or absence of the marking at each of the said positions, obtaining a sequence of bits or electrical signals which identifies the marking made on the concealed surface of the plate.

2. An apparatus for identifying materials and equipment by means of ultrasonic waves, according to claim 1, characterized in that the marking on the concealed surface of the plate is made with a series of blind holes preferably with a concave bottom.

3. An apparatus for identifying materials and equipment by means of ultrasonic waves, in accordance with claim 2, characterized in that the blind holes have a conical or spherical bottom.

4. An apparatus for identifying materials and equipment by means of ultrasonic waves, according to claim 2, characterized in that the plate is fixed in the cavity of a form consistent with that of the plate and adapted to house it and provided in the body of the material to be identified and with a depth which is at least equal to and which is preferably greater than the thickness of the plate to constitute an available space for positioning of the transducers to correspond to the marked positions.

5. An apparatus for the identification of materials and equipment by means of ultrasonic waves according to claim 2, characterized in that the transducer is constructed on a monolith basis according to the arrangement in FIG. 2A with a core consisting of a piezoelectric chip, a coating of conductive metal powder in a resin matrix, a conductor enclosed in a non-conductive prismatic body from which emerges an end of the connector while the other end is electrically connected to the coating, a metallic plate which is part of the piezoelectric chip and which constitutes the earthen conductor, from the part of the piezoelectric chip which is opposite the coating.

6. An apparatus for the identification of materials and equipment by ultrasonic waves according to claim 5, characterized in that placed on the said metal plate is a lens for focusing the ultrasonic beam emitted by the transducer to the depth of the bottom of the bore.

7. An apparatus for identifying materials and equipment by ultrasonic waves according to claim 6, characterized in that the plurality of transducers are grouped together to form a multiple transducer in accordance with an arrangement consistent with that of the marking positions on the plate so that there is opposite each marking position a transducer, according to the diagram shown in FIG. 2B.

8. An apparatus for the identification of materials and equipment by ultrasonic waves according to claim 7, characterized in that in the perimetral part of the multiple transducer there are spacing elements which lean on the visible face of the plate to ensure the desired distance between it and the focusing lens.

9. An ultrasonic identification method applied to materials and equipment using the apparatus according to claim 8, characterized in that the transducers are firstly positioned to correspond to each marking position on the plate so that the transducers are energized by an electrical signal to emit an ultrasonic signal to the plate which is reflected between the body of the plate and which returns to the transducer to restore an electrical signal according to a specific time gate differentiated according to whether the marking is absent or present, the said electrical signal being measured as the difference in voltage or potential between the terminal and the plate of each transducer.

10. A method of using ultrasonic waves to identify materials or equipment according to claim 9, characterized in that the value 1 is allocated to the signal or bit the amplitude value of which is greater than a threshold value determined in the calibration of the transducer while the value 0 is allocated to the signal or bit the amplitude value of which is less than the said threshold value.

11. A method of using ultrasonic waves to identify materials and equipment in accordance with claim 9, characterized in that while using markings with a concave bottom, the ultrasonic signal is dispersed to give a reflected signal of an amplitude which is less than the threshold value.

12. A method of using ultrasonic waves for identification of material and equipment in accordance with claim 9, characterized in that using flatbottomed markings and markings with a bottom parallel to the surfaces of the plate, the return signal due to reflection of the ultrasonic signal on the bottom of the hole is recorded at a time gate other than that of the signal which is reflected on the other hand on the concealed face of the plate and which therefore makes it possible to identify the surface on which the signal is reflected and on the basis of the time gate at which it is present, to distinguish the bit equal to 1 from the bit equal to 0.

13. A method of using ultrasonic waves to identify materials and equipment according to claim 9, characterized in that the correct functioning of the transducers is checked by monitoring whenever the return signal at the time gate corresponding to the reflection on the visible surface of the plate assumes an amplitude value which is greater than the threshold value.

14. A method of using ultrasonic waves for the identification of materials and equipment according to claim 9, characterized in that the positioning of the multiple transducer to correspond to the plate is carried out by allowing a free space between lenses and the visible face of the plate which is filled by a gel adapted to conduct ultrasonic waves, the said gel being applied prior to the positioning of the transducer.

15. A method of using ultrasonic waves to identify materials and equipment according to claim 9, characterized in that one or more marking positions are used to monitor the correct positioning of the multiple transducer in respect of the plate.

16. A method of using ultrasonic waves to identify materials and equipment according to claim 9, characterized in that the recording of the reflected signals is carried out in sequence and by electronic scanning.

17. A method of using ultrasonic waves to identify materials and equipment according to claim 9, characterized in that the reflected signals are recorded by a multiplex technology, switching the transducers which constitute the multiple transducer.

18. A method of using ultrasonic waves to identify materials and equipment according to claim 9, characterized in that the recording of the reflected signals is carried out by properly timed gathering of the return signals from the transducer in order to set up the material identification sequence.

* * * * *